(12) United States Patent
Hintze et al.

(10) Patent No.: US 6,861,011 B1
(45) Date of Patent: Mar. 1, 2005

(54) PROCESS FOR PREPARING METHYLLITHIUM

(75) Inventors: Mark J. Hintze, Charlotte, NC (US); Jing Q. Wen, Gastonia, NC (US)

(73) Assignee: Chemetall Foote Corporation, Kings Mountain, NC (US)

( * ) Notice: Subject to any disclaimer, the term of this patent is extended or adjusted under 35 U.S.C. 154(b) by 0 days.

(21) Appl. No.: 10/703,768

(22) Filed: Nov. 7, 2003

(51) Int. Cl.$^7$ .............................. C02F 1/02; C09K 3/00
(52) U.S. Cl. ........................ 252/182.3; 252/182.12; 252/182.14; 502/153; 502/156; 502/157; 260/665 G; 260/665 R
(58) Field of Search ..................... 252/182.3, 182.12, 252/182.14; 502/153, 156, 157; 260/665 R, 665 G

(56) References Cited

U.S. PATENT DOCUMENTS

| | | | | |
|---|---|---|---|---|
| 4,976,886 A | * | 12/1990 | Morrison et al. | 252/182.3 |
| 5,100,575 A | * | 3/1992 | Hatch et al. | 252/182.3 |
| 5,141,667 A | * | 8/1992 | Morrison et al. | 252/182.3 |
| 5,171,467 A | * | 12/1992 | Mehta et al. | 252/182.3 |
| 5,523,447 A | * | 6/1996 | Kamienski et al. | 556/466 |

* cited by examiner

Primary Examiner—Joseph D. Anthony
(74) Attorney, Agent, or Firm—Fulbright & Jaworski L.L.P.

(57) ABSTRACT

Methyllithium is prepared by reacting chloromethane with a dispersion lithium metal in an aromatic organic solvent with methyltetrahydrofuran.

4 Claims, 16 Drawing Sheets

PROCESS FOR PREPARING METHYLLITHIUM

FIELD OF THE INVENTION

The present invention relates methyllithium solutions made from dispersions of lithium in an aromatic liquid containing methyltetrahydrofuran (MeTHF) by adding liquid or gaseous chloromethane to react with the lithium, thereby forming methyllithium.

BACKGROUND OF THE INVENTION

Organolithium compounds, e.g., butyllithium, are known to be produced by preparing a lithium or lithium/sodium metal dispersion in an inert organic liquid, and then adding a suitable alkyl halide which reacts with the lithium metal to form the organolithium product.

Generally, methyllithium was prepared by reacting chloromethane with two equivalents of lithium metal giving the product and lithium chloride.

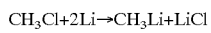

Classically, this reaction was performed in pure diethylether(DEE) as the solvent. However, unlike other alkyllithiums such as butyllithium, sec-butyllithium and tert-butyllithium, methyllithium is insoluble in pure hydrocarbon solvents. Diethyl ether, however, presents a serious potential for fire and explosions and is not a desirable solvent for industrial-scale reactions. Tetrahydrofuran (THF) is a more desirable ether because of it lower vapor pressure and lower autoignition temperature, but MeLi is unstable in pure THF. Methyllithium reacts with an equivalent of THF which then undergoes an irreversible fragmentation reaction.

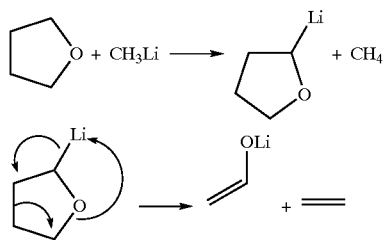

U.S. Pat. Nos. 4,976,886 and 5,141,667 disclose a process for producing organometallic compositions by reacting an organohalide with a mixture of two metals, one being an alkali metal, and the other being selected from magnesium, calcium, barium and zinc in a hydrocarbon solvent containing 0.5 to 2.0 moles of a Lewis Base per mole of organohalide. Methyltetrahydrofuran is disclosed a possible Lewis Base. The '667 patent also claims a method of preparing a stable methyllithium solution by adding a methyl halide to a mixture of lithium metal and an aromatic hydrocarbon containing tetrahydrofuran (THF) in an amount not exceeding 2 moles of THF per mole of methyl halide while maintaining the mixture at a temperature not exceeding 50° C. to react in an inert atmosphere the lithium metal and methyl halide to produce methyllithium and by-product lithium halide.

It has now been discovered that use of MeTHF with an aromatic solvent yields methyllithium compositions which are more stable than corresponding THF preparations when prepared as described herein.

SUMMARY OF THE INVENTION

Methyllithium is prepared by dispersing lithium metal in an aromatic organic solvent with from 2 to 4 equivalents of MeTHF per equivalent of MeLi and adding liquid or gaseous chloromethane under conditions where the chloromethane reacts with the lithium metal to form methyllithium. The resultant methyllithium solutions contains the aromatic organic, MeTHF and MeLi, along with byproducts, if any. In preferred embodiments, sodium metal is added to the dispersion in an amount of up to 50% by weight of the metals, preferably from 1–25% and more preferably from 3–5% by total weight of the metals. In particularly preferred embodiments, a lithium dispersion in an organic solvent is previously prepared and used as the source of lithium.

For purposes of the present invention, the inert organic liquid used in preparing the first or second lithium dispersions, in the order they are produced according to the method of the invention, are any suitable C5–C10 organic alkyls or cycloalkyls which are not reactive with lithium but is suitable for performing a reaction with an alkyl halide to produce the desired alkyllithium product. Hexane, cyclohexane and heptane are preferred.

The dispersions may be prepared by heating lithium metal in the inert organic liquid in the presence of a dispersing agent to a temperature above the melting point of lithium metal, or the higher of both lithium and another metal, e.g., sodium metal, to melt the metals. The dispersing agent is preferably an organic compound, typically a fatty acid or combination thereof, that aids in dispersing the metal. Linseed oil is particularly preferred, although other agents may be used, e.g, oleic acid, stearic acid, peanut oil. Agitation or shear force is then applied to disperse the molten metal in the form of droplets or flakes to disperse the lithium metal and form the lithium dispersion. It is preferred that the dispersing agent is present as 0.3 to 0.65 % of the combined weight of the inert organic material, lithium and optionally sodium metal, and the dispersing agent.

If sodium metal is present, it is preferred that the weight ratio of lithium to sodium ranges from 20:1 to 1:1, most preferably from 18:1 to 1.2:1.

The lithium dispersions of the invention may be prepared in an apparatus which is also part of the invention. The apparatus has a disperser and an exchange tank which communicate with each other via a feed pipe. Alternatively, two or more separate feed pipes may be in communication with the disperser and the exchange tank.

The disperser has an inlet therein suitable for receiving the lithium and optionally sodium metals, preferably in ingot form. Of course, other forms of metal may be used, such as ground, comminuted, or other raw forms of the metal. In an alternative embodiment, melted metal is added to the inert organic liquid which is heated to maintain the metal in molten state. The inert organic liquid and the dispersing agent may also be charged to the disperser via the inlet, but typically a separate liquid inlet is provided, which is in communication with a tank containing the inert organic material and/or the dispersing agent. Typically the disperser and the exchange tank are closed vessels so that a non-reactive atmosphere can be provided by introduction of an inert gas, e.g., argon, under pressure.

The disperser is provided with a temperature regulating system to heat or cool the vessel as desired, e.g., to heat the vessel to melt the lithium metal. Importantly, the disperser has an agitator therein to agitate the molten lithium and optionally sodium metal to form the dispersion. The agitator should apply sufficient force so that the mean particle size of the resultant lithium and optionally sodium metal flakes range from 5 to 60 microns, preferably from 10 to 55 microns, and most preferably from 30–50 microns.

An exchange tank is provided to remove the inert organic liquid and replace or exchange it for a second inert organic liquid. The second inert organic liquid may be the same or different than the first, but has the same characteristics described herein. The exchange is typically done by filtration, and a suitable filter mechanism is also provided.

Transfer of the dispersion from the disperser to the exchange tank may be accomplished by pressurizing the disperser with an inert gas.

The lithium dispersion are preferably used in preparing methyllithium according to the present invention, although any lithium or lithium/sodium dispersions may be used. In preferred embodiments, the appropriate amount of lithium metal dispersion (or lithium sodium metal dispersion) is added to the aromatic solvent and MeTHF mixture. Chloromethane is then added as a liquid or gas under conditions that allow reaction with the lithium metal to form methyllithium. In preferred embodiments, the aromatic organic compound is toluene (also known as methylbenzene, toluol and phenylmethane), ethylbenzene (also known as ethylbenzol, phenylethane and EB), or Cumene (also known as isopropylbenzene, 1-methylethyl)benzene or 2-phenylpropane).

DETAILED DESCRIPTION

Methyllithium solutions are made from dispersions of lithium in an aromatic liquid containing methyltetrahydrofuran (MeTHF) by adding liquid or gaseous chloromethane to react with the lithium, thereby forming methyllithium. The MeTHF is present in an amount of from 2 to 4 equivalents based on methyllithium, and preferably from more than 2 equivalents up to and including 4 equivalents.

Surprisingly, MeTHF formulations have been found to be more stable than corresponding THF formulations.

The initial lithium dispersion is preferably prepared by melting lithium and optionally another metal, e.g., sodium, in an inert organic liquid and agitating the mixture to form the dispersion. The inert organic liquid is preferably a C5–C10 n-alkane, preferably C7–C8. Most preferred are heptane, hexane and cyclohexane.

Figure 1A:
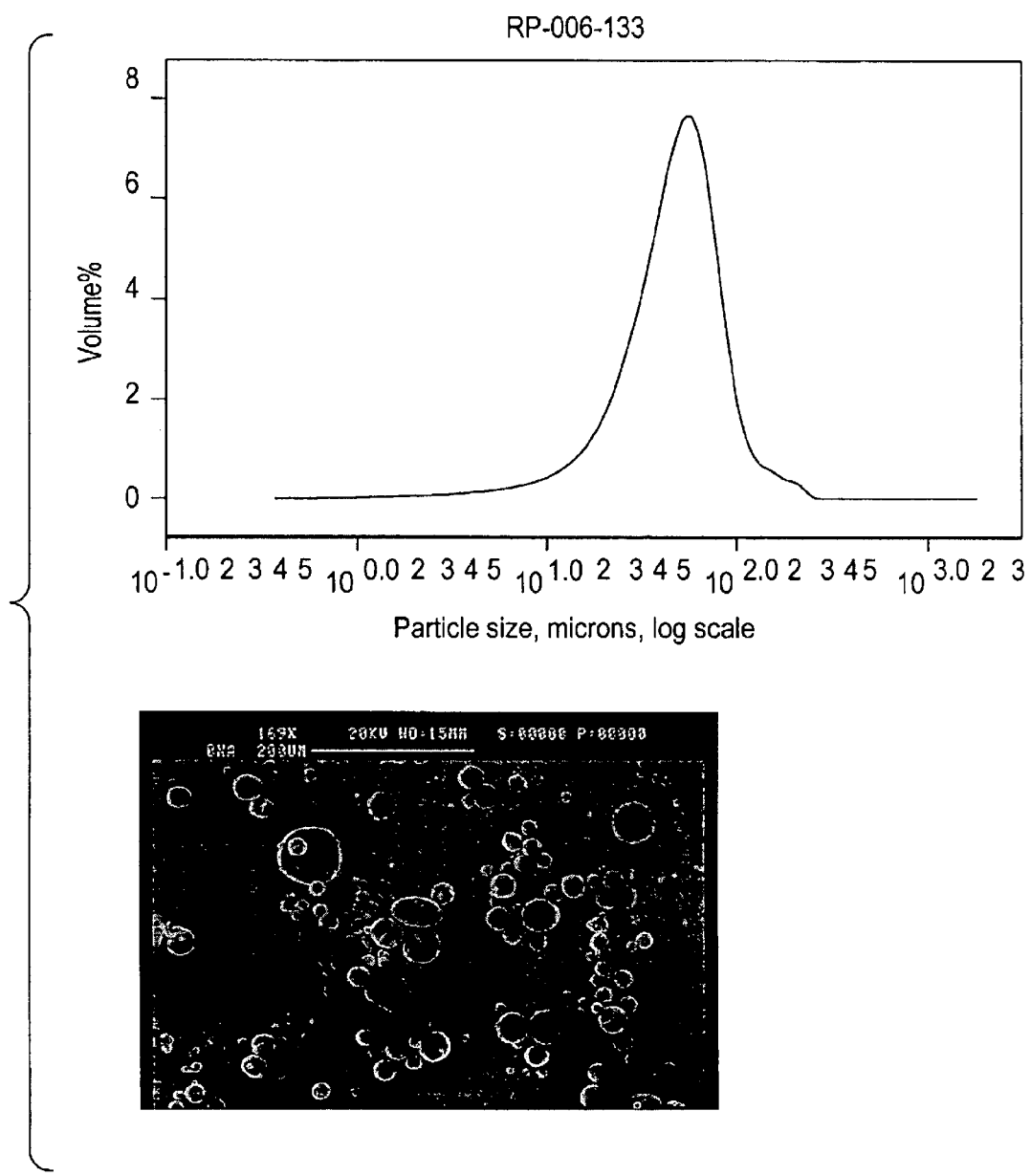
FIGS. 1a–3d are particle size traces and scanning electron micrographs (SEM's) of lithium and/or sodium metal particles of the dispersions according to the present invention and relate to the corresponding Example (e.g., FIG. 1a corresponds with Example 1a, etc.).
Figure 1B:
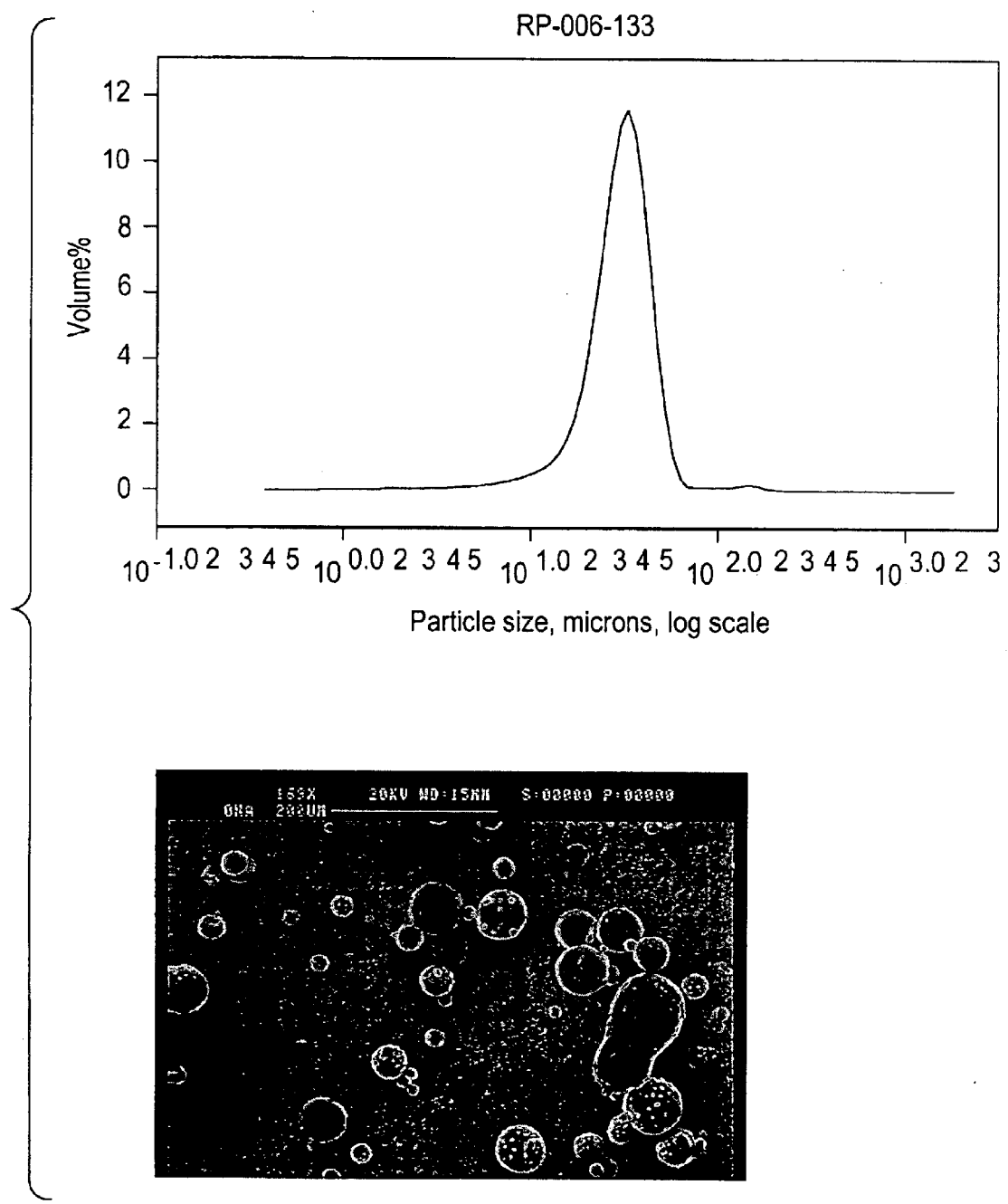
Figure 1C:
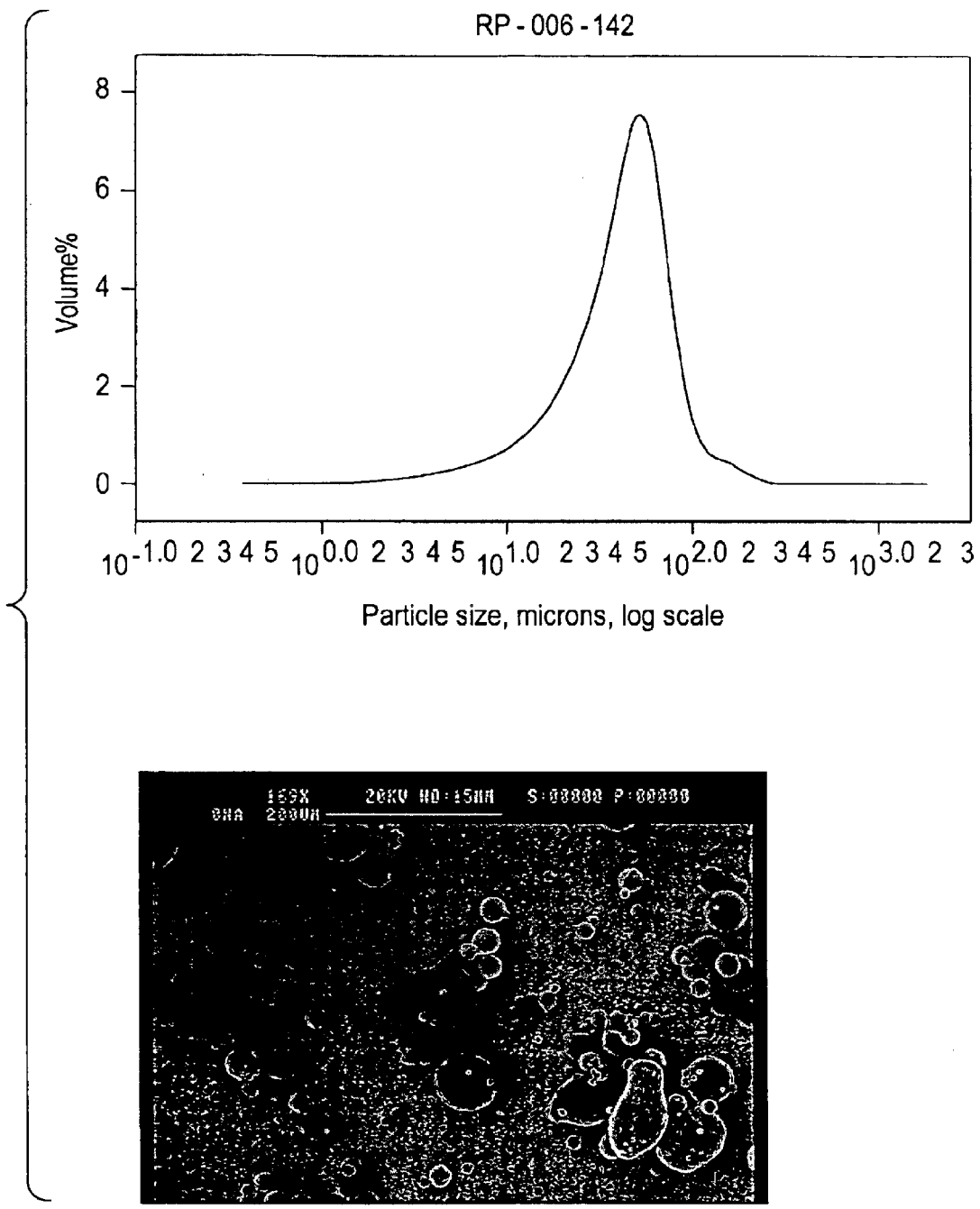
Figure 1D:
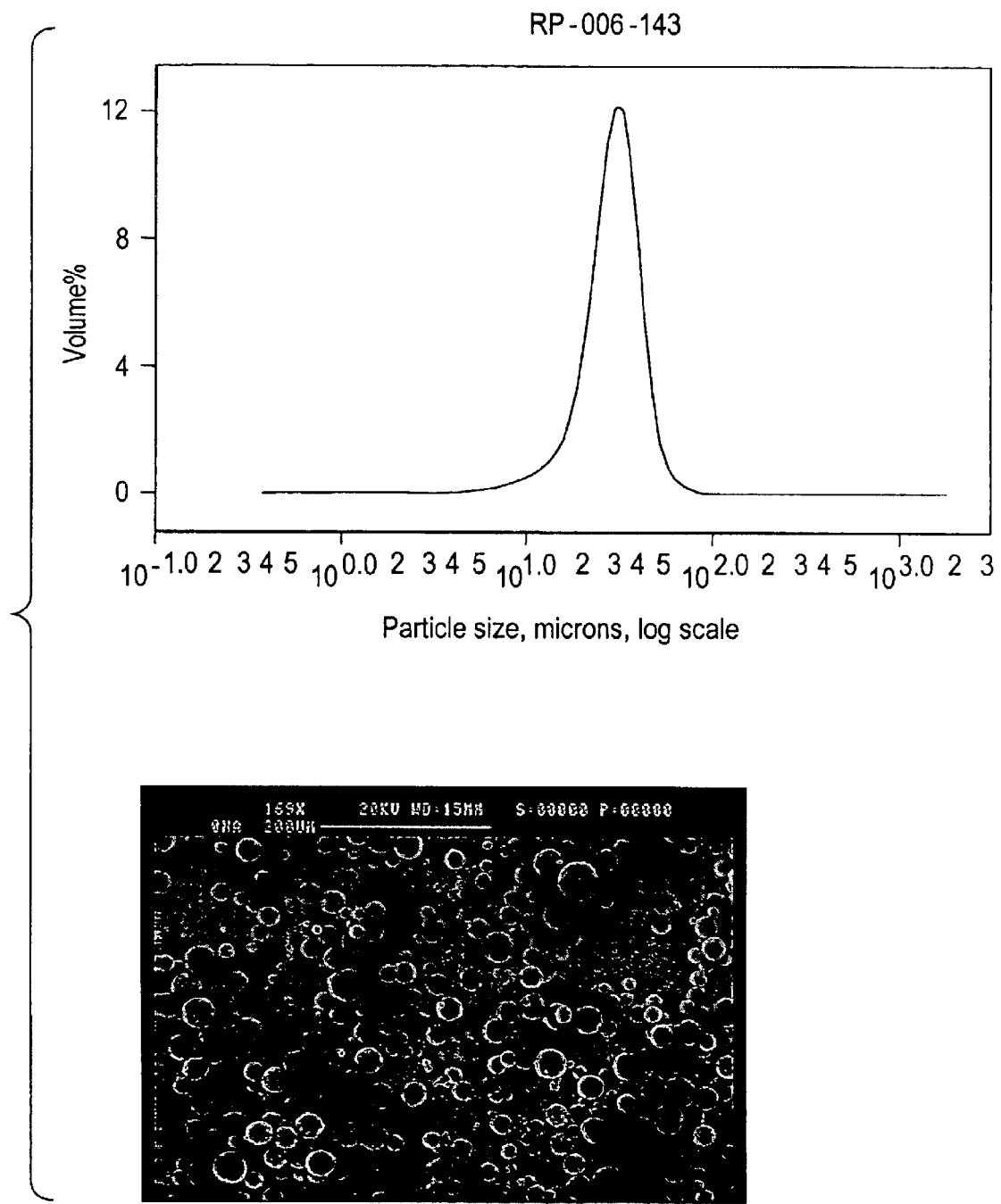
Figure 2A:
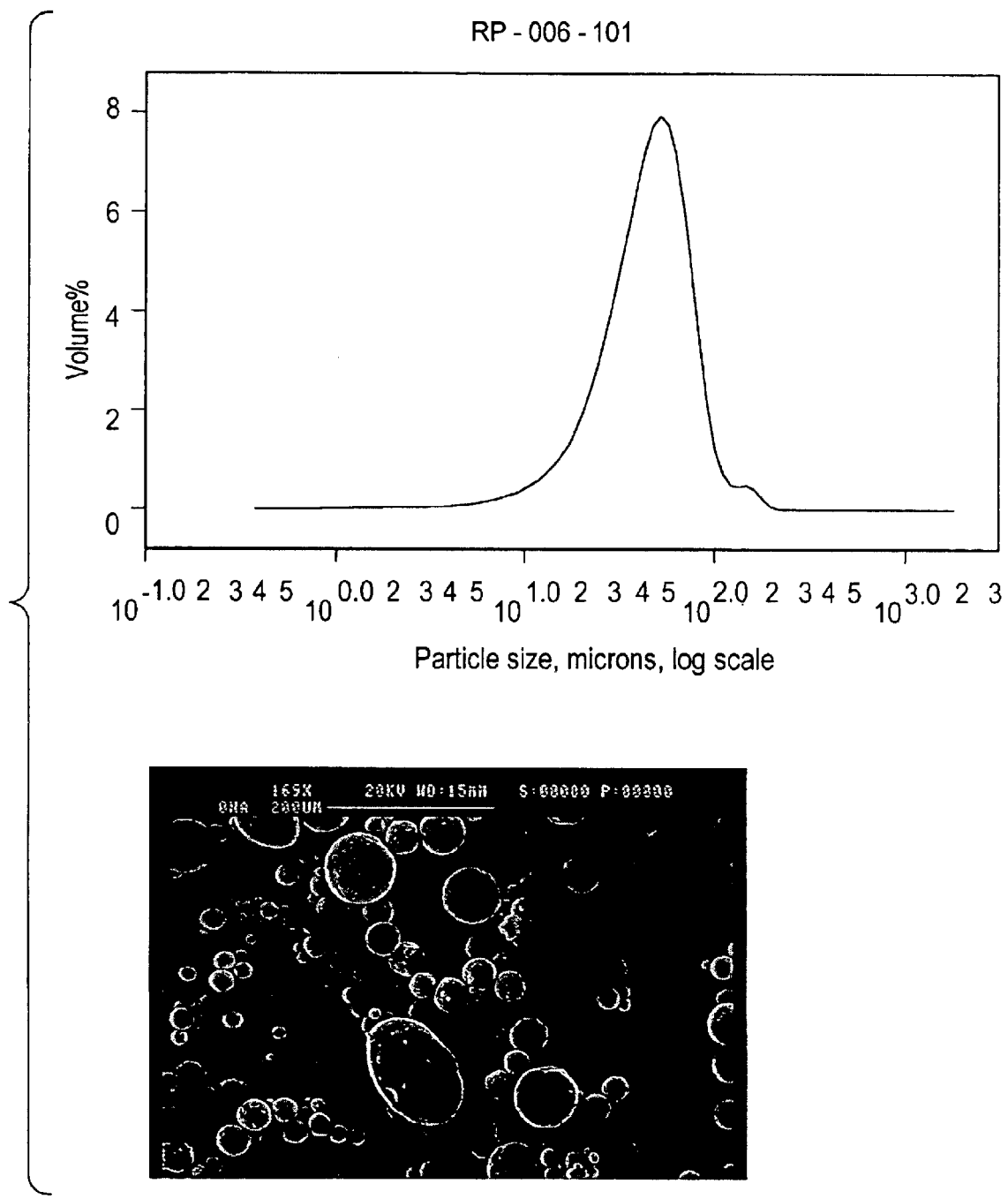
Figure 2B:
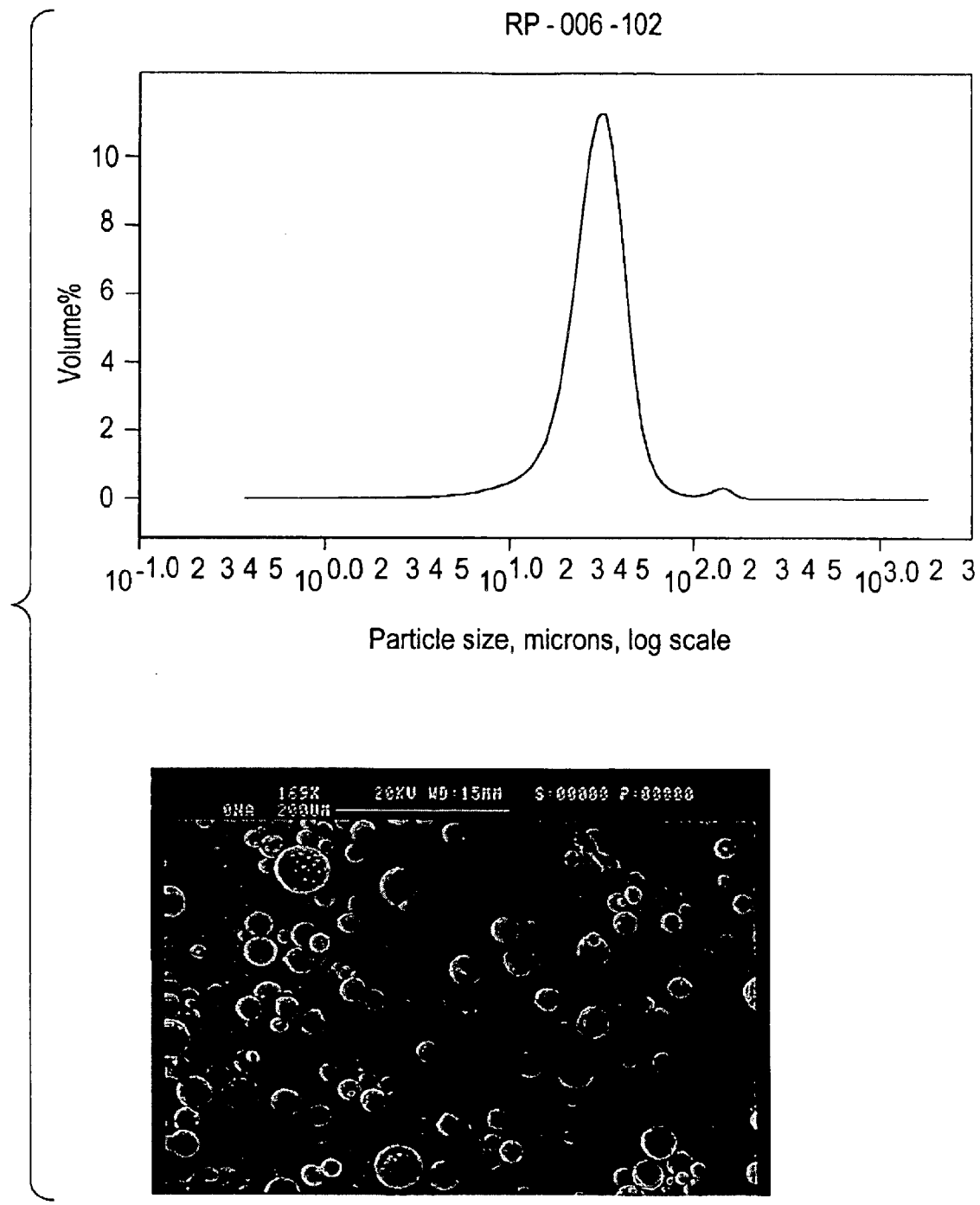
Figure 2C:
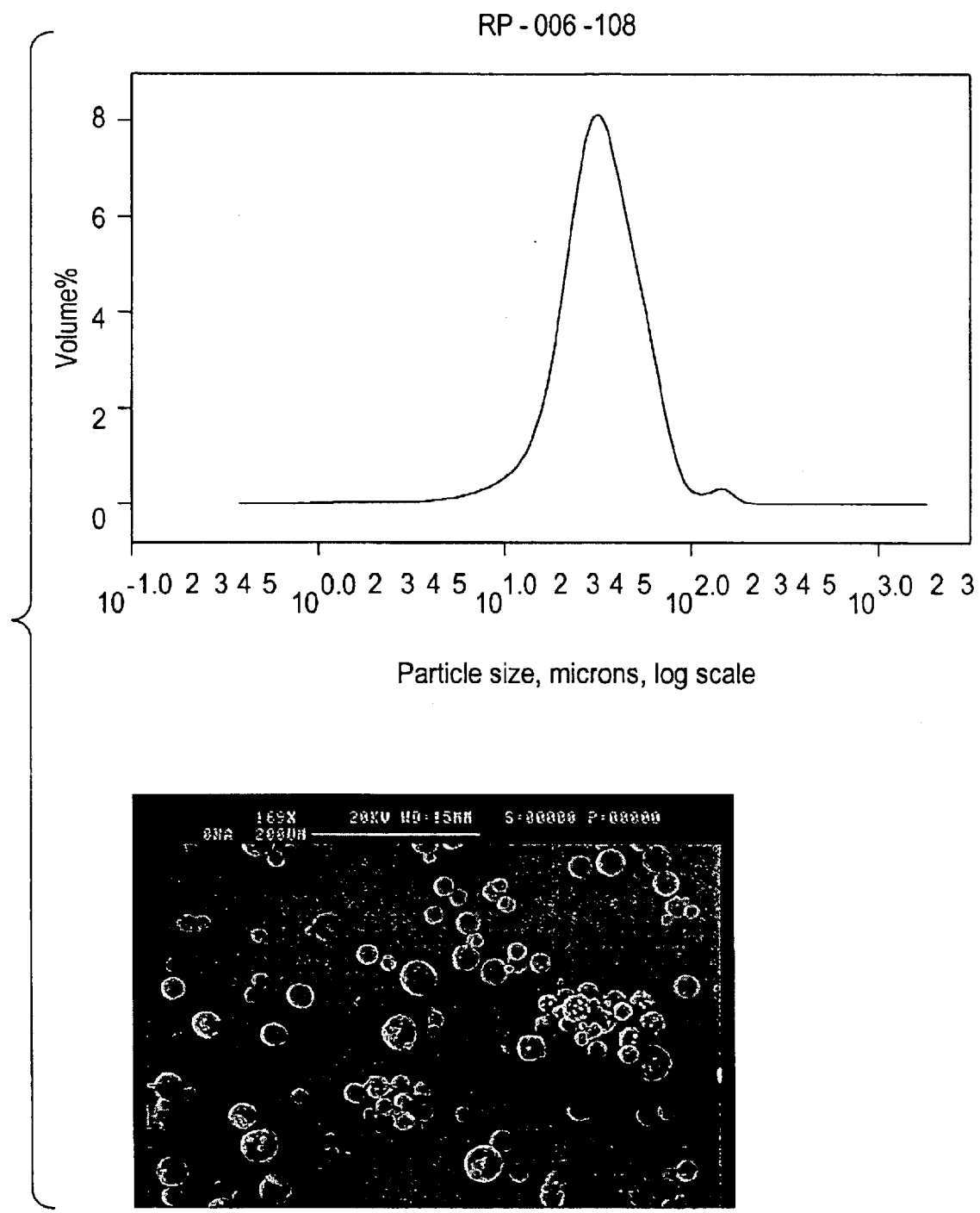
Figure 2D:
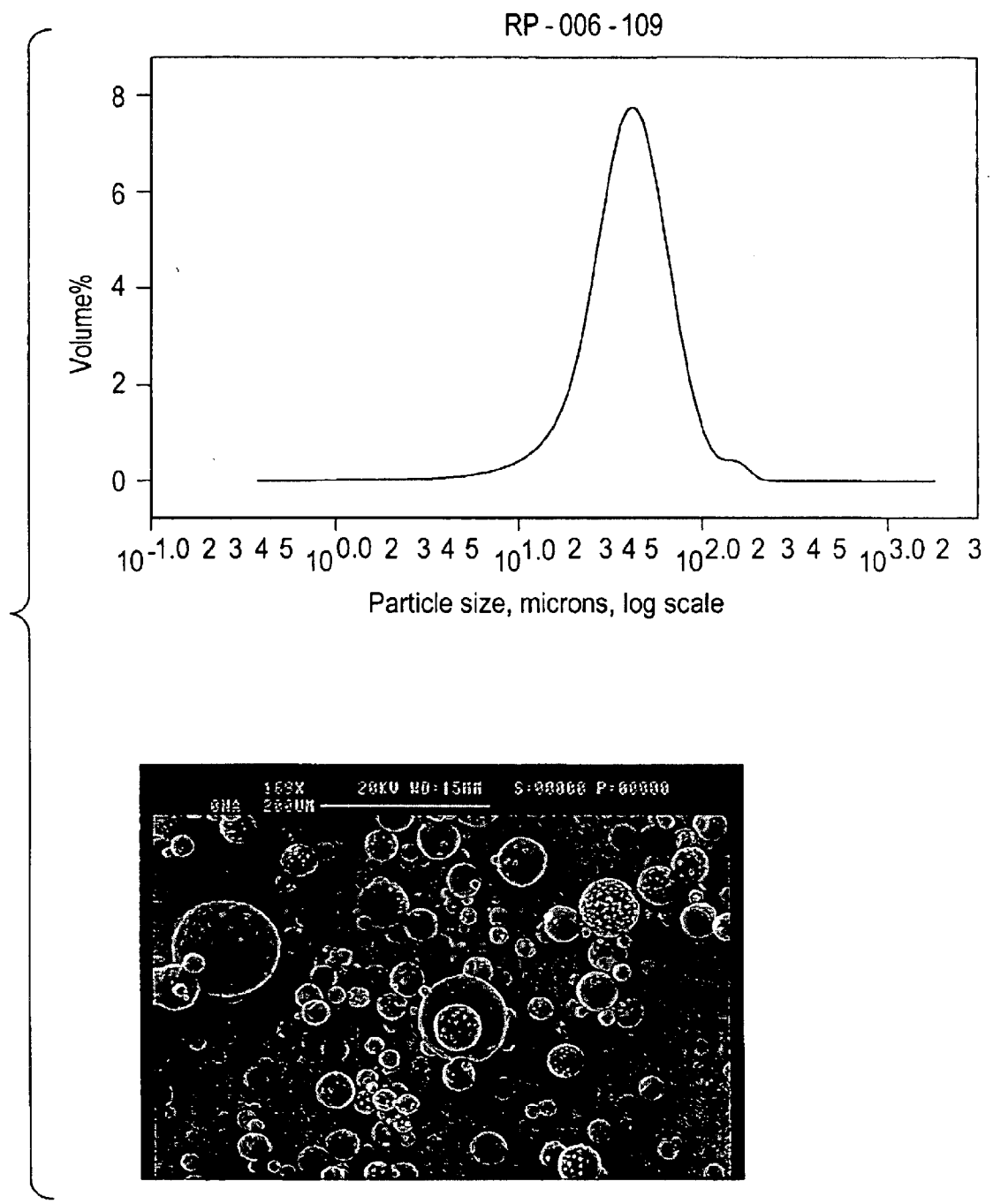
Figure 3A:
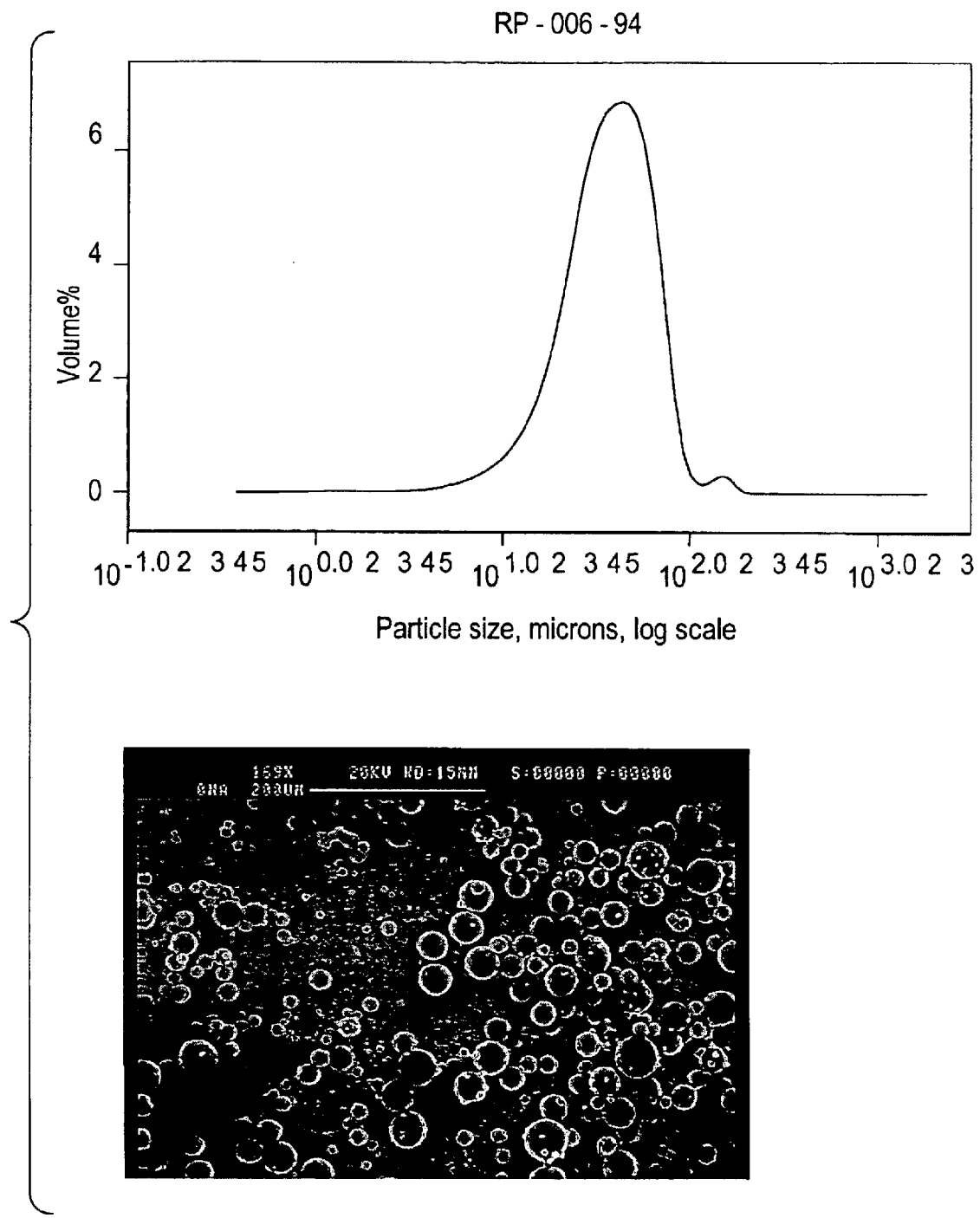
Figure 3B:
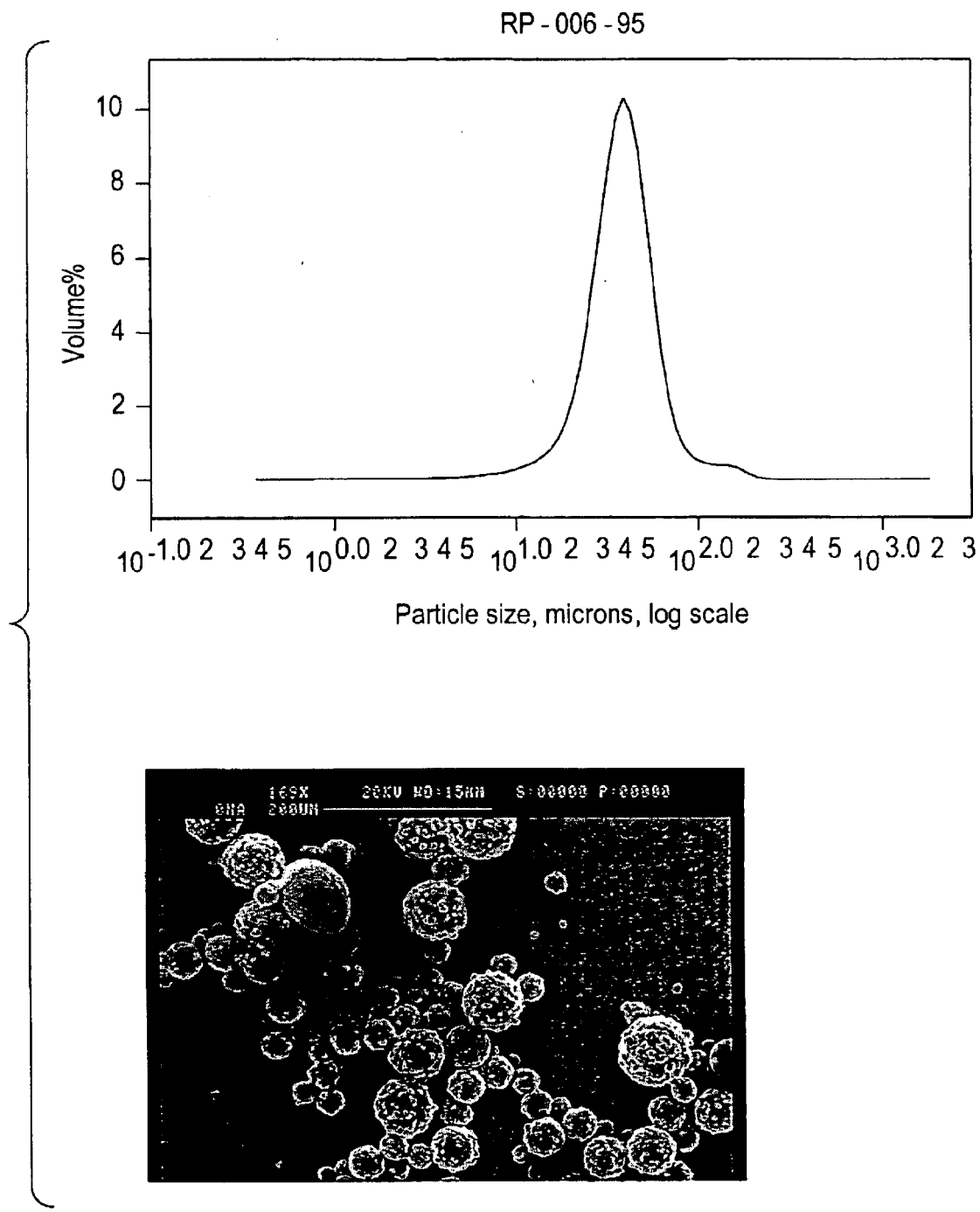
Figure 3C:
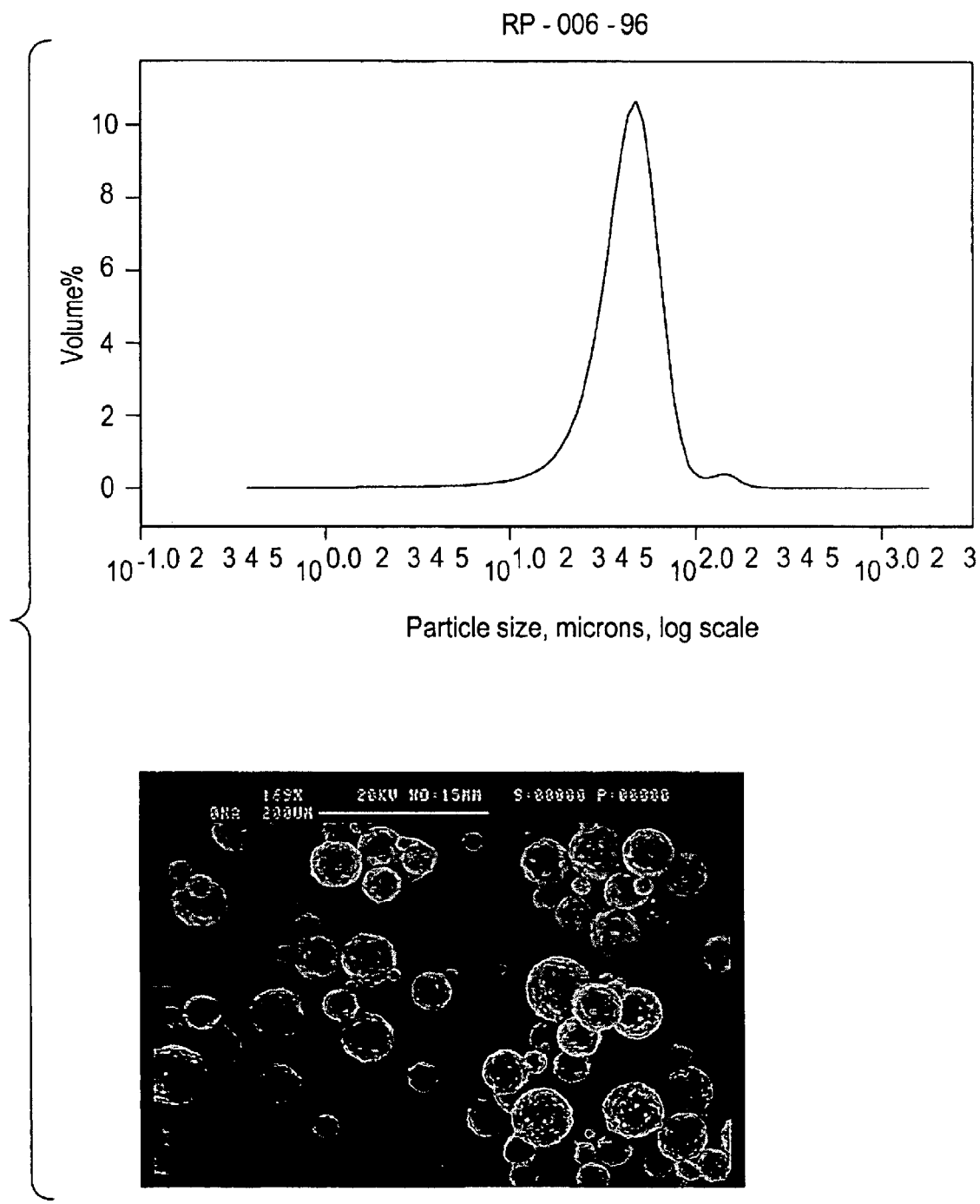
Figure 3D:
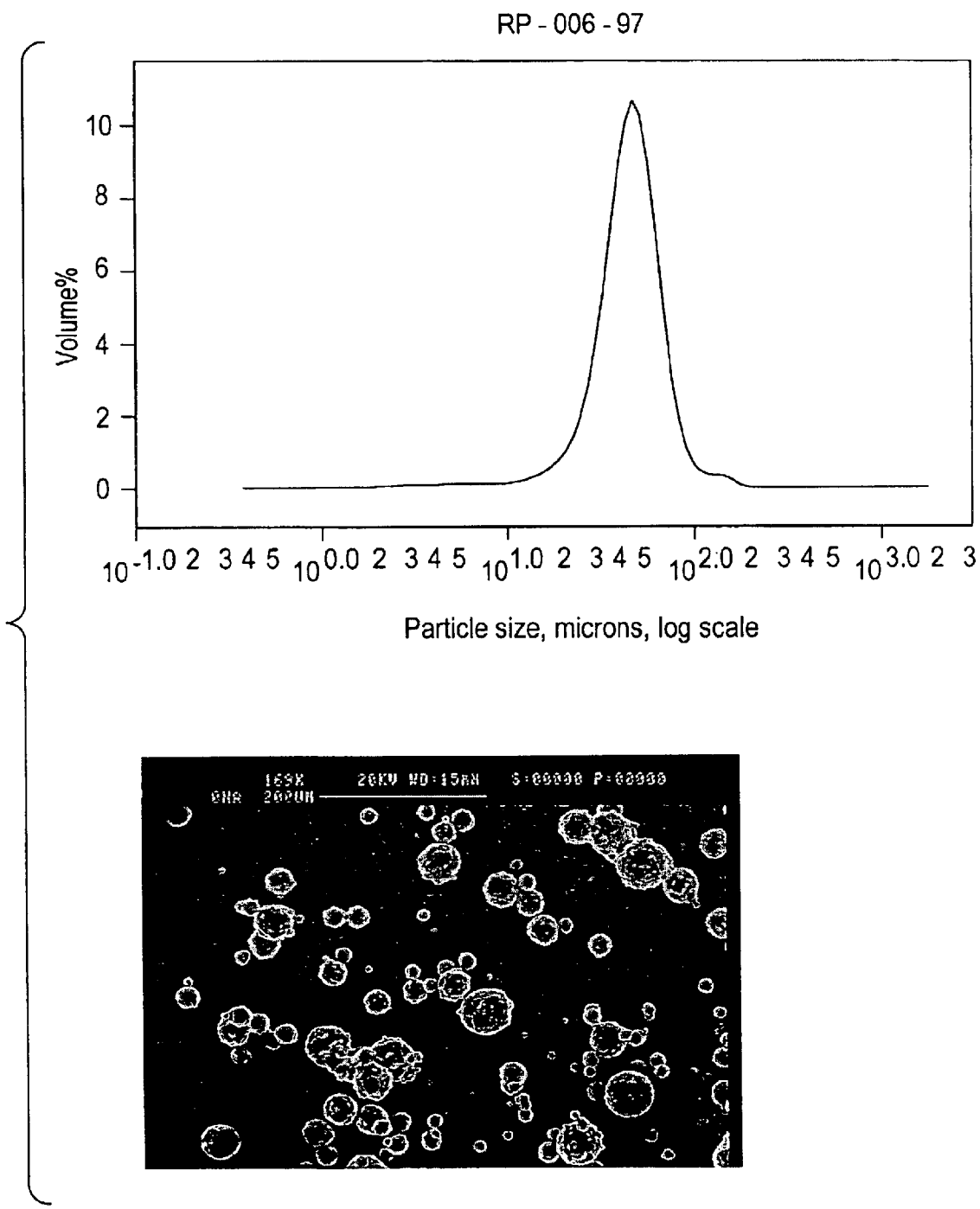
Figure 4:
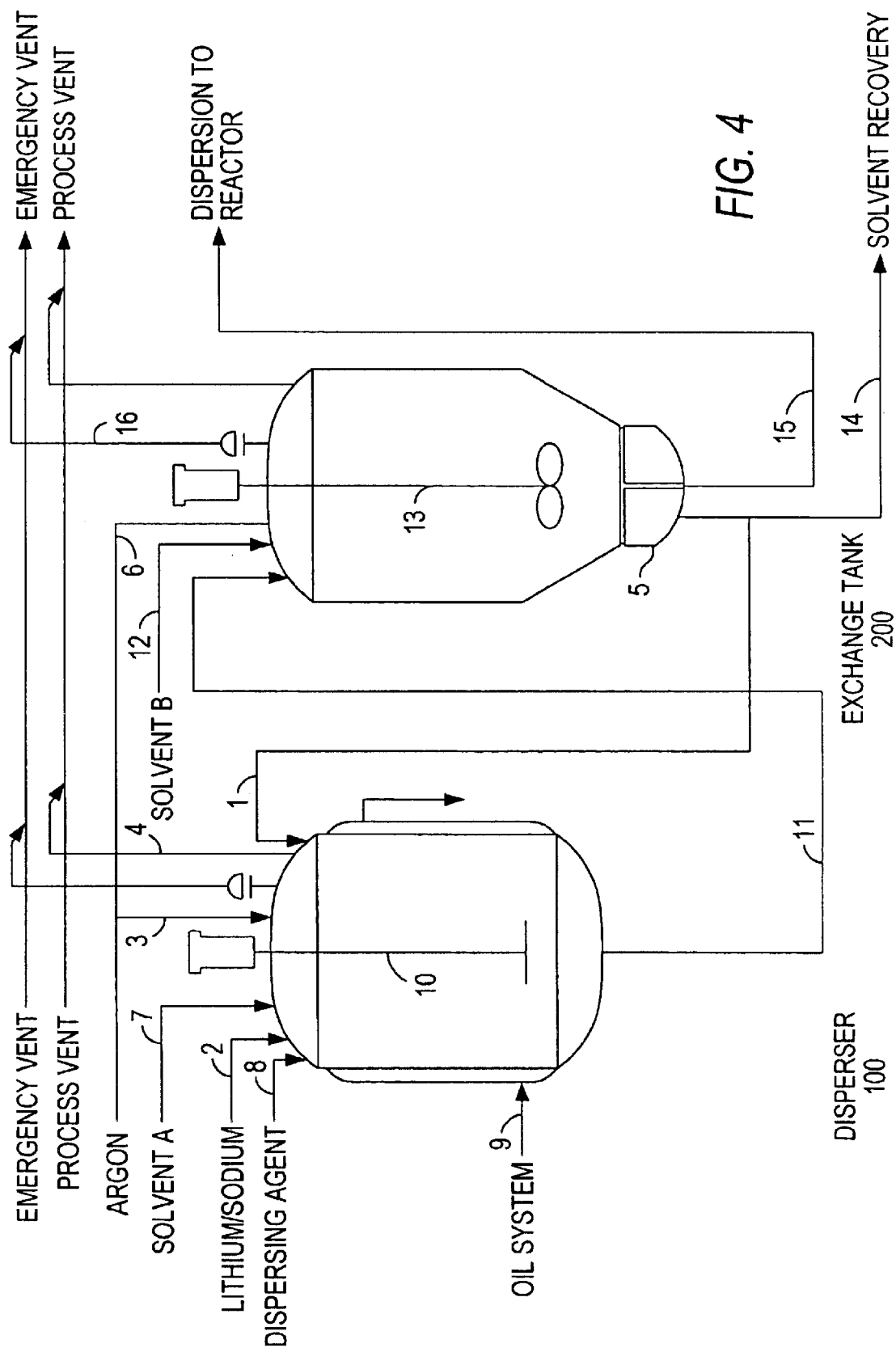
FIG. 4 is a process flow diagram which also details the apparatus of the invention.

Referring to FIG. 4, the two primary vessels of the apparatus are dispersion vessel 100 and exchange tank 200. The desired mix of lithium metal and, if added, sodium metal is charged into disperser 100 via solid inlet feed 2, which is closeable to maintain the internal atmosphere. Preferably, dispersion vessel 100 is enclosed to maintain an inert gas atmosphere, e.g., argon which is provided via gas inlet 3. Solid inlet feed 2 is closed after dispersion vessel is charged with the metal, and vent line 4 is opened so that any vapors present can be displaced as solvent filtration from the exchange tank 200 to the disperser 100 is completed.

A suitable volume of inert organic liquid 1 is added to disperser 100, e.g., recirculated from a previous batch, by blowing the inert organic liquid 1 from dish 5 of exchange tank 200 back to disperser 100 by applying an inert gas pressure on exchange tank 200. Disperser 100 is inspected through charging port 2 to ensure that all of the inert organic liquid (designated A in FIG. 4) from the previous batch in exchange tank 200 is filtered back to disperser 100. An additional volume of inert organic liquid 7 is added to the disperser 100 if the volume is not sufficient. Dispersing agent 8 is added to aid in dispersing the lithium and other metals. Linseed oil is a preferred dispersing agent, such as the refined linseed oil commercially available from Reichold Chemical (product code 144491-00 and CAS number 8001-26-1). The specification items and range for this Reichold product include a Gardner color of from 0.0 to 6.0, an Acid Value-NV of from 0.0 to 0.3, and a specific gravity at 25° C. of from 0.926 to 0.930. Preferably, the weight ratio of dispersing agent to total weight of the dispersion, including the metals, is from 0.25 to 0.3%. Disperser vessel 100 is then closed, vent line 4 is closed, and argon or another inert gas is applied via gas inlet 3. Preferably, 10 to 20 psig inert gas is applied.

Disperser 100 is heated via a heating/cooling system 9, preferably an oil system, controlled by temperature controller 18, to approximately 390° F., or the melting point of the metal or metals, at which point the internal pressure is about 180 psig when heptane is used. Once the desired temperature is reached, dispersion agitator 10 is started to disperse the molten lithium and optionally sodium metals. A preferred agitator (motor, frame, shaft, seal, and blade) is the Morehouse Cowles Inc 10 D Cowles Dissolver. The blade is part number B07A00 as determined from Morehouse Cowles Drawing 4-55435-B. The preferred blade has the following characteristics: 7¼ inch diameter maximum, measured from outer edge of tooth to outer edge of tooth; and 18 teeth, half directed upward, half downward. Each tooth is 1¼" long, ⅜" deep at the outer edge. Each tooth is angled 30 degrees from the tangent of the blade circle. The blade rotates counterclockwise when viewed from the top of disperser 100. The outer edge of each tooth trails. Although the aforementioned is preferred, any available agitator that can yield a lithium dispersion having the desired mean particle size of 5 to 60 microns, may be used.

After the charged materials have reached the melting point of the metals, the agitator is started at low speed, e.g., about 1,425 rpm. Once it is determined that all of the lithium and optionally sodium is melted, disperser agitator 10 is switched to a relatively high speed above, e.g., 3,450 rpm, causing high shear agitation and forming the dispersion. This generally takes several minutes, e.g., three to five minutes. Heating/cooling system 9 is then adjusted to cool the dispersion and agitation is stopped. The dispersion is cooled, preferably to approximately 140° F., thus causing the dispersed, molten particles to solidify. Optionally, agitation may again be applied on both low and high speed to ensure even mixing of the dispersion prior to transfer to exchanger tank 200. The dispersion is then transferred via transfer pipe 11 by pressurization of disperser 100. Following transfer, a solvent rinse 7 is made ("tail") through disperser 100 and transfer pipe 11 until transfer is complete. Dispersion agitator 10 is then stopped.

Filtration or screening 17 is then begun to separate the metals, now in the form of spheres or spheroids, from the inert organic liquid/dispersing agent. This is accomplished by, e.g., applying pressure 6 with an inert gas, e.g., argon, on exchange tank 200. When filtration is complete, the lithium sodium mix is rinsed by applying argon pressure 6 on exchange tank 100, with the desired volume of a second inert organic liquid, which may be the same or different as the inert organic liquid forming the dispersion, and the mixture is agitated with exchange tank agitator 13 to resuspend the solids in the new organic liquid. Typically the second organic liquid is hexane. Following agitation 13 the rinsing solvent is filtered ("screened") 14 to a solvent recovery process. The dispersed metal mixture is then repulped in the exchange tank by starting the applicable solvent pump and metering the desired volume of the second inert organic liquid 12, into the exchange tank, and agitating 13. The dispersed metal, now rinsed with the second organic liquid is transferred via second transfer pipe 15 to reactor 300 by pressurizing exchange tank 200 by adding pressurized inert gas to the exchange tank via inlet 6. A solvent flush 12 of the second organic liquid is applied to clear the transfer line and to ensure a complete transfer. Exchange tank 200 is then depressurized via line 16 in preparation to receive the next quantity of the first lithium dispersion from disperser 100.

In reactor 300 the chloromethane is added to the lithium dispersion to form the methyllithium. Since methylchloride is a gas above a temperature of −24 C. degrees, the chloromethane may be charged to the reactor as a gas so contact the surface of the lithium dispersion/aromatic/MeTHF mixture or the chloromethane may be cooled and added to the mixture as a liquid.

The chloromethane is added in an amount such that there are 2 to 4 equivalents of MeTHF per equivalent of MeLi produced. Preferably, greater than 2 up to 4 equivalents of MeTEF are present, and more preferably from 2.1 to 3 equivalents.

A catalyst may be added to assist the reaction. Suitable temperature, pressure, and other operating parameters are provided to facilitate the reaction, and these will vary with the desired reactants and end product.

If gaseous chloromethane is used, then the operating parameters will range from 1–10 atmospheres, and preferably from 1 to 5 atmospheres, of chloromethane are used, and an inert gas is also introduced to prevent reaction of the product with oxygen or atmospheric moisture.

If liquid chloromethane is used, then gaseous chloromethane is introduced into a condenser and cooled to a temperature at which the chloromethane liquefies, e.g., about −40° C. is sufficient. The liquid chloromethane is then added to the lithium metal/MeTHF/aromatic solvent mixture and allowed to react and form MeLi. The reaction is exothermic, so it is preferable to control the temperature by cooling the reaction vessel.

Preferred aromatic organic solvents include toluene, cumene and ethylbenzene, with cumene being particularly preferred.

The resultant solutions contain the MeLi, from 2–4 equivalents of MeTHF, the aromatic solvent and any byproducts or sodium, if present. Preferably, 2 equivalents of MeTHF are used in the formulations, as these are generally more stable then 3 or 4 equivalent formulations.

The resultant products preferably lose less than about 5–6% of the starting MeLi to decomposition after storage at 30 days at 40° C. when measured by $^1$H NMR compared to 14% in corresponding compositions in which the MeTHF is replaced with THF.

Preferred Embodiments

1. Preferred Lithium Dispersions

The lithium dispersion of the invention is prepared by melting lithium and optionally another metal, e.g., sodium, in an inert organic liquid and agitating the mixture to form the dispersion. The inert organic liquid is preferably a C5–C10 n-alkane, preferably C7–C8. Most preferred are heptane, hexane and cyclohexane.

Referring again to FIG. 4, the two primary vessels of the apparatus are dispersion vessel 100 and exchange tank 200. The desired mix of lithium and sodium metal is charged into disperser 100 via solid inlet feed 2, which is closeable to maintain the internal atmosphere. Preferably, dispersion vessel 100 is enclosed to maintain an inert gas atmosphere, e.g., argon which is provided via gas inlet 3. Solid inlet feed 2 is closed after dispersion vessel is charged with the metal, and vent line 4 is opened so that any vapors present can be displaced as solvent filtration from the exchange tank 200 to the disperser 100 is completed.

A suitable volume of inert organic liquid 1 is added to disperser 100, e.g., recirculated from a previous batch, by blowing the inert organic liquid 1 from dish 5 of exchange tank 200 back to disperser 100 by applying an inert gas pressure on exchange tank 200. Disperser 100 is inspected through charging port 2 to ensure that all of the inert organic liquid (designated A in FIG. 4) from the previous batch in exchange tank 200 is filtered back to disperser 100. An additional volume of inert organic liquid 7 is added to the disperser 100 if the volume is not sufficient. Dispersing agent 8 is added to aid in dispersing the lithium and other metals. Linseed oil is a preferred dispersing agent, such as the refined linseed oil commercially available from Reichold Chemical (product code 144491-00 and CAS number 8001-26-1). The specification items and range for this Reichold product include a Gardner color of from 0.0 to 6.0, an Acid Value-NV of from 0.0 to 0.3, and a specific gravity at 25° C. of from 0.926 to 0.930. Preferably, the weight ratio of dispersing agent to total weight of the dispersion, including the metals, is from 0.25 to 0.3%. Disperser vessel 100 is then closed, vent line 4 is closed, and argon or another inert gas is applied via gas inlet 3. Preferably, 10 to 20 psig inert gas is applied.

Disperser 100 is heated via a heating/cooling system 9, preferably an oil system, controlled by temperature controller 18, to approximately 390° F., or the melting point of the metal or metals, at which point the internal pressure is about 180 psig when heptane is used. Once the desired temperature is reached, dispersion agitator 10 is started to disperse the molten lithium and optionally sodium metals. A preferred agitator (motor, frame, shaft, seal, and blade) is the Morehouse Cowles Inc 10 D Cowles Dissolver. The blade is part number B07A00 as determined from Morehouse Cowles Drawing 4-55435-B. The preferred blade has the following characteristics: 7¼ inch diameter maximum, measured from outer edge of tooth to outer edge of tooth; and 18 teeth, half directed upward, half downward. Each tooth is 1¼" long, ⅜" deep at the outer edge. Each tooth is angled 30 degrees from the tangent of the blade circle. The blade rotates counterclockwise when viewed from the top of disperser 100. The outer edge of each tooth trails. Although the aforementioned is preferred, any available agitator that can yield a lithium dispersion having the desired mean particle size of 5 to 60 microns, may be used.

After the charged materials have reached the melting point of the metals, the agitator is started at low speed, e.g., about 1,425 rpm. Once it is determined that all of the lithium and optionally sodium is melted, disperser agitator 10 is switched to a relatively high speed above, e.g., 3,450 rpm, causing high shear agitation and forming the dispersion. This generally takes several minutes, e.g., three to five minutes. Heating/cooling system 9 is then adjusted to cool the dispersion and agitation is stopped. The dispersion is cooled, preferably to approximately 140° F., thus causing the dispersed, molten particles to solidify. Optionally, agitation may again be applied on both low and high speed to ensure even mixing of the dispersion prior to transfer to exchanger tank 200. The dispersion is then transferred via transfer pipe 11 by pressurization of disperser 100. Following transfer, a solvent rinse 7 is made through disperser 100 and transfer pipe 11 until transfer is complete. Dispersion agitator 10 is then stopped.

Filtration or screening 17 is then begun to separate the metals, now in the form of spheres or spheroids, from the inert organic liquid/dispersing agent. This is accomplished by, e.g., applying pressure 6 with an inert gas, e.g., argon, on exchange tank 200. When filtration is complete, the lithium sodium mix is rinsed by applying argon pressure 6 on exchange tank 100, with the desired volume of a second inert organic liquid, which may be the same or different as the inert organic liquid forming the dispersion, and the mixture is agitated with exchange tank agitator 13 to resuspend the solids in the new organic liquid. Typically the second organic liquid is hexane. Following agitation 13 the rinsing solvent is filtered 14 to a solvent recovery process. The dispersed metal mixture is then repulped in the exchange tank by starting the applicable solvent pump and metering the desired volume of the second inert organic liquid 12, into the exchange tank, and agitating 13. The dispersed metal, now rinsed with the second organic liquid is transferred via second transfer pipe 15 to reactor 300 by pressurizing exchange tank 200 by adding pressurized inert gas to the exchange tank via inlet 6. A solvent flush 12 of the second organic liquid is applied to clear the transfer line and to ensure a complete transfer. Exchange tank 200 is then depressurized via line 16 in preparation to receive the next quantity of the first lithium dispersion from disperser 100.

In reactor 300 the desired organic reactant, typically an alkyl halide, is added to the lithium dispersion to form the desired organolithium end product. For example, if methyllithium is desired, chloromethane is added. A catalyst may be added to assist the reaction. Suitable temperature, pressure, and other operating parameters are provided to facilitate the reaction, and these will vary with the desired reactants and end product. For example, to prepare butylithium, a reaction temperature of 50 degrees Celsius and a pressure of 0 to 20 psig are preferred.

The lithium alkyl product may be subsequently recovered by use of a filter vessel after a reactor vessel. The remaining portion may be recycled to recover solvent and any remaining lithium, sodium and chloride for reprocessing.

It should be noted for purposes of the present invention that the lithium particles may not be perfectly spheroidal but are nominally spherical in shape, however egg-shaped and ovoid particles are also formed.

EXAMPLES OF PREFERRED EMBODIMENTS

Lithium dispersion are prepared with different ratios of lithium and sodium.

Example 1 (a–d)

The lithium or lithium sodium dispersions can be used to make perferred embodiments of the methyllithium dispersions of the present invention. They may also be used to make other alkyllithium products, for example, dispersions used for the production of n-butyllithium in hexane (NBH) are prepared as follows:

The following amounts of ingredients are charged to a disperser:

| | |
|---|---|
| Lithium | 66 lbs |
| Sodium | 55 lbs |
| Heptane used in Disperser | 70 gallons or 385 lbs |
| Linseed Oil | 1,500 ml or 3.04 lbs |

The disperser is heated to a temperature sufficient to melt the metals. Agitation is commenced at a speed of approximately 1425 rpm, and increased to 3450 rpm to produce a dispersion having lithium and sodium droplets averaging from 10–60 microns in size as determined by a Coulter LS230 laser diffraction unit with kerosene. The quantity of linseed oil reflects the amount which would be used if the entire 70 gallons of heptane was virgin heptane.

Most of the heptane used to prepare the dispersion is supplied from a previous dispersion batch. Typically, 65 gallons of heptane are screened back, roughly 5 gallons are lost to evaporation, and 5 gallons is added to make up the difference (virgin heptane). When heptane is recycled, typically only 750 mls of linseed oil are used. To calculate the weight of linseed oil, use the numbers provided above. Optimally, 0.61 wt. % of the entire mass in the disperser is linseed oil in this Example.

The quantity of linseed oil shown above reflects that amount which would be used if the entire 70 gallons of heptane is new (virgin) heptane. However, if most of the heptane that is used to prepare a dispersion is screened/filtered back from a previous dispersion batch which had been moved forward to the exchange tank (typically 65 gallons of heptane are screened back and about 5 gallons are lost to vaporization) then typically 5 gallons of virgin heptane would need to be added to the disperser to provide the desired volume. When heptane is recycled back, which is typically the case, only 750 ml of linseed oil are used because some linseed oil is already in the filtered heptane. That is, it has been discovered that, the concentration of linseed oil in the dispersion should be approximately 0.60 wt % of the entire mass in the disperser, although this may vary, and is preferably from 0.5 to 1.0 wt %. The amount of linseed oil used will vary depending on many factors, including the ratio of lithium to sodium, the solvents used, and other factors known to those skilled in the art.

The dispersion is then transferred to the exchange tank where the heptane/linseed oil are removed from the metal spheres and spheroids, and the metals are washed with hexane, and then resuspended in approximately 50 gallons of hexane. The hexane/lithium dispersion is then used to make alkyllithium products. Dispersers 1–5 are the same but are added provided to improve production flow.

Example 2 (a–d)

Dispersion used for the production of n-butyllithium in cyclohexane (NBC) are prepared as follows:

The following amounts of ingredients are charged to a disperser:

| | |
|---|---|
| Lithium | 72 lbs |
| Sodium | 40 lbs |
| Heptane used in Disperser | 70 gallons or 385 lbs. |
| Linseed Oil | 1,500 ml or 3.04 lbs |

The quantity of linseed oil, the screening/filtration and reuse of the heptane, and the temperature and speeds of agitation used in the disperser, are the same as in Example 1.

The dispersion is then transferred to the exchange tank where the heptane/linseed oil are removed from the metal spheres and spheroids, and the metals are washed with cyclohexane, and then resuspended in approximately 50 gallons of cyclohexane. The cyclohexane/lithium dispersion is then used to make alkyllithium products.

Example 3 (a–d)

Dispersions used for the production of sec-butyllithium in cyclohexane (SEC) are prepared as follows:

The following amounts of ingredients are charged to a disperser:

| | |
|---|---|
| Lithium | 36 lbs |
| Sodium | 5 lbs |
| Heptane used in Disperser | 70 gallons or 385 lbs. |
| Linseed Oil | 1,500 ml or 3.04 lbs. |

The quantity of linseed oil, and screening/filtration and reuse of the heptane, and the temperature and speeds of agitation used in the disperser, are the same as in Example 1.

The dispersion is then transferred to the exchange tank where the heptane/linseed oil are removed from the metal spheres and spheroids, and the metals are washed with cyclohexane, and then resuspended in approximately 50 gallons of cyclohexane. The cyclohexane/lithium dispersion is then used to make alkyllithium products.

Lithium dispersions prepared according to Examples 1, 2 and 3 were prepared using either cyclohexane or hexane as the second organic liquid. The mean particle size of the lithium particles was determined using a Coulter LS230 laser diffraction unit with kerosene.

Samples are prepared for particle size analysis as follows:

a) Equipment 1-1 mL syringe fitted with 18G needle and flushed with argon 1-10 mL syringe fitted with 20G needle flushed with argon containing 2 mL kerosene 1-10 mL syringe fitted with long needle flushed with argon containing 5 mL hexane 1-stainless steel filter holder with teflon O-ring and gasket, dried 1-0.4 um nylon filter, dried 3-9.5 dram vials (hexane, sonication, waste) with lids or septa, dried rubber septa, transfer pipettes b) Experimental A 0.2 mL sample is drawn into a 1-mL syringe fitted with an 18G needle. Approximately 2.5 mL dry hexane is then drawn into the syringe. The sample/hexane mixture is filtered through a 0.4 micron nylon filter in a stainless steel filter holder. A 10 mL syringe half full of dry hexane and half full of dry argon is used to force hexane and argon through sample. A 10 mL syringe filled with 2 mL dry kerosene and 8 mL dry argon is used rinse the sample in the filter holder with kerosene and argon. Approximately 1 mL argon is left in the syringe. The filter holder is opened and the teflon O-ring is removed. The filter is removed and put in a 9.5 dram vial with approximately 7 to 10 mL dry kerosene. Three (3) drops of Aerosol-OTS surfactant is added and the sample is sonicated for 10 minutes. The filter is removed from vial with forceps and the sample is sonicated for ten additional minutes. When sample is done sonicating the entire sample is put in a particle sizer for about 5 seconds, and the pump is then turned off. Three runs should be done consecutively. After runs are complete the sample is rinsed out of particle sizer. Data is analyzed with Fraunhoffer model.

A summary of the particle size analysis for twelve individual dispersions is given in Table 1.

TABLE 1

Summary of particle size analysis.

| Example | Product | Disperser | mean particle size, microns | min part size, microns | max part size, microns |
|---|---|---|---|---|---|
| 1a | nbh | 2 | 52.69 | 0.375 | 282.1 |
| 1b | nbh | 4 | 33.62 | 0.375 | 234.1 |
| 1c | nbh | 2 | 50.64 | 0.375 | 309.6 |
| 1d | nbh | 4 | 31.66 | 0.375 | 92.09 |
| 2a | nbc | 5 | 51.77 | 0.721 | 234.1 |
| 2b | nbc | 4 | 33.89 | 0.721 | 213.2 |
| 2c | nbc | 3 | 38.71 | 0.721 | 213.2 |
| 2d | nbc | 5 | 45.66 | 0.375 | 282.1 |
| 3a | sbc | 1 | 42 | 0.5 | 213.2 |
| 3b | sbc | 2 | 44.28 | 0.7 | 234.1 |
| 3c | sbc | 4 | 48.88 | 0.721 | 256.8 |
| 3d | sbc | 5 | 45.76 | 0.721 | 213.2 | nbh - n-butyllithium in hexane
nbc - n-butyllithium in cyclohexane
"sbc" is sec-butyllithium in cyclohexane FIGS. 1a through 3d contain particle size graphs and micrographs for the twelve individual dispersions.

Figure 5B:
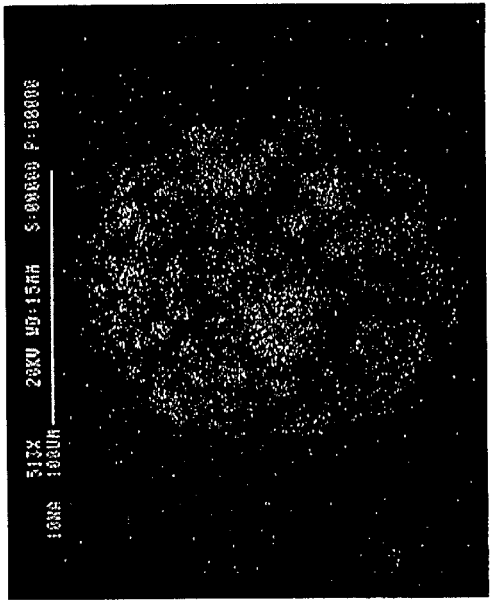
FIG. 5B (right) is a sodium dot map of the large droplet shown in FIG. 5A.
Figure 5A:
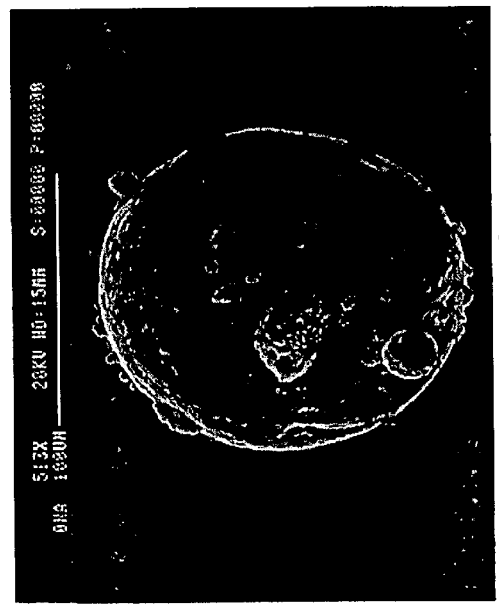
FIG. 5A (left) is an SEM of a sodium/lithium droplet from a dispersion prepared according to the present invention.

FIG. 5A is an SEM of a lithium/sodium prepared according to the present invention using 74.8 lb Li and 33.0 lb Na. FIG. 5B is a sodium dot map of the droplets shon in FIG. 5A.

Figure 6B:
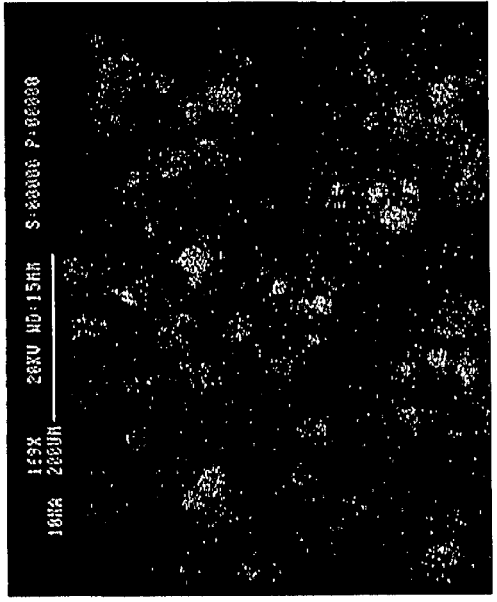
FIG. 6B (right) is a sodium dot map of those droplets.
Figure 6A:
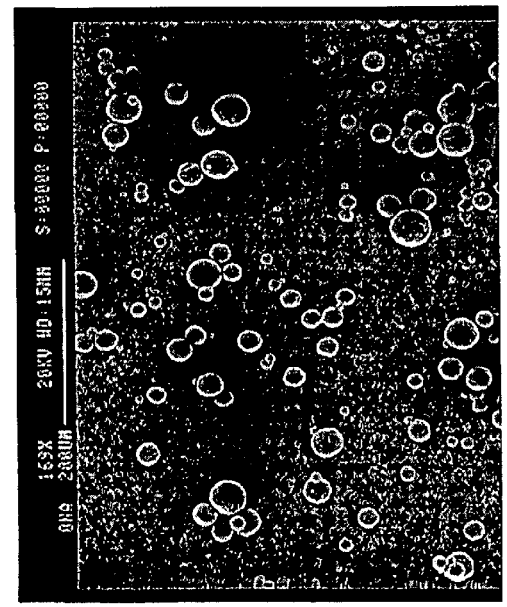
FIG. 6A (left) is an SEM of another sample of sodium/lithium droplets according to the present invention.

FIG. 6A is an SEM of a lithium/sodium droplets prepared using 74.2 lb Li and 33.4 lb Na. FIG. 6B is a sodium dot map of those droplets. For the samples in FIG. 5 and FIG. 6, both the micrographs and dot maps were performed on the same respective sample and in the same sample chamber. Micrographs were recorded with a Cambridge 240 SEM and stored in bitmap format. Dispersions were prepared for SEM by diluting the dispersion in dry hexane, passing it through a silver syringe mounted filter, and purging with argon to evaporate residual solvent. The SEM chamber was back-filled with argon and the samples were transferred to the chamber through an argon glove bag attached to the front of the sample chamber.

Other metals such as potassium and others that form a solid heterodisprsion with lithium at the operating temperatures provided herein may be used in accordance with the invention to replace all or some of the sodium component.

2. Examples of Preferred Methyllithium Compounds and Methods

Table 1 shows the series of MeLi solutions that were prepared and analyzed

TABLE 1

| Storage | | 2 | 3 | 4 | 2 | 3 | 4 | 2 | 3 | 4 | Pure |
|---|---|---|---|---|---|---|---|---|---|---|---|
| | | | | | Equivalents MeTHF | | | | | | |
| 15 days | at 15° C. | x | x | x | x | x | x | x | x | x | x |
| 30 days | | x | x | x | x | x | x | x | x | x | x |
| 15 days | at 40° C. | x | x | x | x | x | x | x | x | x | x |
| 30 days | | x | x | x | x | x | x | x | x | x | x |
| | | | | | Equivalents THF | | | | | | |
| 15 days | at 15° C. | x | | | | | | x | | | |
| 30 days | | x | | | | | | x | | | |
| 15 days | at 40° C. | x | | | | | | x | | | |
| 30 days | | x | | | | | | x | | | |

The first row of the chart shows the three aromatic solvents used, toluene, ethylbenzene, and cumene, along with the reaction done in pure MeTHF. The first column contains the two ether components, Me-THF and THF. Intersections between the first row and column represent MeLi formulations that were prepared. For example, in solutions using Me-THF and Toluene, formulations were prepared with 2, 3 and 4 equivalents of Me-THF per equivalent of MeLi. The amount of the aromatic component was adjusted to maintain the MeLi concentration between 2.8–3.0%. Each formulation was held at 15 and 40° C. and assayed at 15 and 30 days.

Controls were run with THF and toluene and THF and cumene; however, only formulations with two equivalents of THF per equivalent of MeLi were prepared and analyzed. These controls were also held at 15 and 40° C. and assayed at 15 and 30 days.

The general experimental method used to prepare these solutions is as follows: The initial step for each MeTHF/aromatic pair was the preparation of a 600 ml stock solution. This stock solution had a typical concentration of 3.8% MeLi with a 1:1.6 MeLi to MeTHF ratio.

All glassware was oven dried, assembled hot and purged with argon while cooling.

A three-neck, 1 liter round bottom flask with magnetic stir bar and under positive argon pressure was fitted with a thermometer and a jacketed, 125 ml addition funnel topped by a dewar condenser. The flask was charged with the calculated amounts of aromatic solvent (Aldrich Chemical), lithium dispersion (5% sodium) and 2-Methyltetrahydrofuran (Aldrich). The jacketed funnel and condenser were maintained below −40° C. with a dry ice-isopropanol slurry. Chloromethane from a steel cylinder (99.5+%, Aldrich) was introduced, via a brass regulator, into the condenser. A predetermined volume of chloromethane was condensed and collected in the addition funnel. With the contents of the flask at room temperature, the reaction was started with stirring and drop wise addition of chloromethane from the addition funnel. The reaction initiates almost immediately as indicated by a rise in the solution temperature. The temperature of the reaction was controlled between 40–45° C. using an isopropanol/dry ice bath. $^1$H NMR was used to monitor the reaction. The addition period was about 1 hour. After the reaction was judged to be complete, the mixture was transferred to a pressure filter. The LiCl was filtered from the product using argon pressure.

From this stock solution, formulations with 1:2, 1:3 and 1:4 MeLi to MeTHF were made by adding the appropriate amount of MeTHF as determined by $^1$H NMR. A final concentration adjustment was made by adding the aromatic carrier solvent to give a MeLi solution in the range of 2.8–3.0% for each formulation. The two controls: THF/Toluene and THF/Cumene as well as the pure MeTHF case were made using the same general procedure; however, only fine concentration adjustments were necessary since multiple formulations were not required.

Once a particular formulation was completed it was transferred to six oven-dried, argon-purged 2 oz. Qorpak Clear Boston Rounds with TFE-lined closures. Three bottles were placed in a bath at 15±0.2° C. and three were placed in a bath at 40±0.2° C.

The samples prepared in Example 1 were monitored at 15 and 30 days. Each sample was only used one time for analysis. Typically, stability studies of alkyllithium compounds require little more than determining the loss of carbon-bound lithium by the Gilman double titration method or by one of the many direct titration methods now available. Titration as an analytical method proved to be inadequate for MeLi because the aromatic component provides a second route for MeLi decomposition in addition to the route in which MeLi reacts with the ether component.

For example, the THF/Toluene formulations are believed to follow at least the following two decomposition routes:

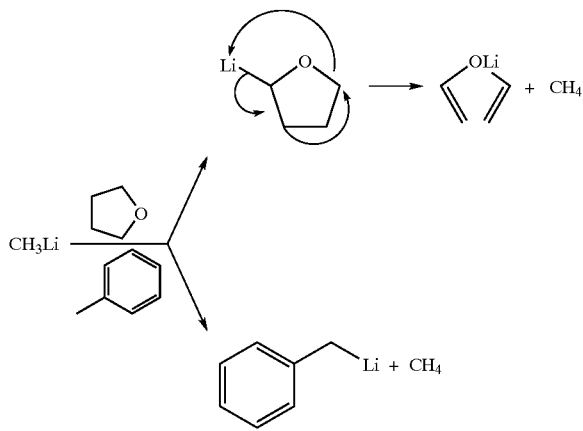

Titration methods cannot distinguish between MeLi and the benzyllithium, since both have carbon bound lithium. $^1$H NMR, however, can easily distinguish between the two lithium species. So, while titrations were performed on all formulations, stability is be based on $^1$H NMR data.

It is believed, without being bound to any particular theory, that because lithiation of the aromatic occurs primarily at the benzylic position, stability would be expected to increase with increasing substitution at that position as shown below.

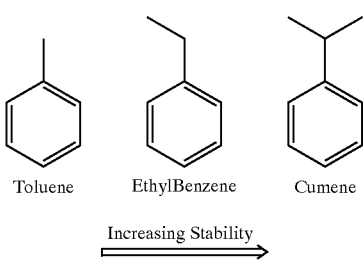

Toluene  EthylBenzene  Cumene

Increasing Stability

Thus, solutions using MeTHF as the ether component should be more stable than those with THF, independent of the aromatic carrier solvent being used. The data below confirm this. Not only does the methyl group sterically hinder the hydrogen at the two position, but it also destabilizes the 2-lithio-2-methyltetrahydrofuran relative to metallating the five position. Therefore, metallation would occur predominately at the five position.

The data in table 3 is for samples stored at 15° C. NMR data is in the first line of each entry for each sample.

TABLE 3

Stability of Methyl Lithium in Different Solvents at 15 C.°

| Solvent | Ether | 0 Day | 15 Days | 30 Days |
|---|---|---|---|---|
| Cumene | 2 × | 2.87% | 2.86%, 0.02% | 3.00%, — |
|  | MeTHF | 2.92% | 2.90%, 0.040% /day | 2.93%, — |
|  | 3 × | 2.87% | 3.00%, — | 3.00%, — |
|  | MeTHF | 3.00% | 2.96%, 0.090% /day | 3.02%, — |
|  | 4 × | 2.80% | 2.82%, — | 2.81%, — |
|  | MeTHF | 2.89% | 2.82%, 0.16% /day | 2.86%, 0.030% /day |
| Ethyl-benzene | 2 × | 2.90% | 3.07%, — | 2.98%, — |
|  | MeTHF | 2.98% | 2.96%, 0.050% /day | 2.98%, — |
|  | 3 × | 3.01% | 2.99%, 0.05% /day | 2.94%, 0.07% |
|  | MeTHF | 2.95% | 2.96%, — | 2.95%, — |
|  | 4 × | 2.94% | 3.04%, — | 2.94%, — |
|  | MeTHF | 2.97% | 2.99%, — | 2.98%, — |
| Toluene | 2 × | 3.00% | 2.82%, 0.43% /day | 2.89%, 0.12% /day |
|  | MeTHF | 2.95% | 2.95%, — | 2.93%, 0.02% /day |
|  | 3 × | 2.86% | 2.88%, — | 2.81%, 0.06% /day |
|  | MeTHF | 2.97% | 2.98%, — | 2.96%, — |
|  | 4 × | 2.92% | 2.65%, 0.66% /day | 2.55%, 0.41% /day |
|  | MeTHF | 2.90% | 2.87%, 0.07% /day | 2.89%, 0.01% /day |
| Toluene | 2 × THF | 2.88% | 2.88%, — | 2.72%, 0.18% /day |
|  |  | 2.80% | 2.76%, 0.10% /day | 2.77%, 0.034% /day |
| Cumene | 2 × | 2.98% | 3.20%, — | 3.04%, — |
|  | MeTHF | 2.99% | 3.02%, — | 3.00%, — |
| MeTHF | MeTHF | 2.94% | 2.84%, 0.24% /day | 2.78%, 0.16% /day |
|  |  | 2.82% | 2.72%, 0.25% /day | 2.69%, 0.15% /day |

(Methyl lithium concentration and rate of decomposition by $^1$H NMR and active titration)

The relative error in an NMR measurement is roughly 5%. Samples that have a higher final concentration than initial fall within this margin of error and can be interpreted as having undergone negligible decomposition. Generally it can be seen in table 3 that 15° C. is too low of a temperature to differentiate between formulations using cumene or ethylbenzene regardless of how many equivalents of MeTHF were used. The control using cumene and two equivalents of THF also showed no loss of activity over the thirty day test period.

All formulations using toluene showed decomposition. However, little if any difference was observed between the Toluene with two equivalents of MeTHF and the control sample of toluene with two equivalents THF. Their relative stability was the same for this low storage temperature and thirty day test period.

Finally, the pure MeTHF sample showed a decomposition similar to the toluene formulations.

In contrast to the 15° C. data, 40° C. gave an accelerated decomposition rate which resulted in very clear, systematic results. The 40° C. data is presented in table 4; however the results are better appreciated in graphical form.

TABLE 4

Stability of Methyllithium in Aromatic Solvents at 40 C.° (Methyl lithium concentration and rate of decomposition by $^1$H NMR and active titration)

| Solvent | Ether | 0 Day | 15 Days | 30 Days |
|---|---|---|---|---|
| Cumene | 2 × | 2.87% | 2.64%, 0.53% | 2.69%, 0.19% /day |
|  | MeTHF | 2.92% | 2.85%, 0.16% /day | 2.82%, 0.14% /day |
|  | 3 × | 2.87% | 2.68%, 0.44%/day | 2.59%, 0.31%/day |
|  | MeTHF | 3.00% | 2.82%, 0.40% /day | 2.74%, 0.26% /day |
|  | 4 × | 2.80% | 2.52%, 0.67% /day | 2.10%, 0.69% /day |
|  | MeTHF | 2.89% | 2.59%, 0.69% /day | 2.33%, 0.59% /day |
| Ethyl-benzene | 2 × | 2.90% | 2.92%, 0.13% /day | 2.68%, 0.32% /day |
|  | MeTHF | 2.98% | 2.93%, 0.11% /day | 2.83%, 0.16% /day |
|  | 3 × | 3.01% | 2.73%, 0.66% /day | 2.49%, 0.56% /day |
|  | MeTHF | 2.95% | 2.76%, 0.46% /day | 2.63%, 0.35% /day |
|  | 4 × | 2.94% | 2.63%, 0.75% /day | 2.12%, 0.90% /day |
|  | MeTHF | 2.97% | 2.62%, 0.84% /day | 2.30%, 0.73% /day |
| Toluene | 2 × | 3.00% | 2.24%, 1.81% /day | 1.81%, 1.28% /day |
|  | MeTHF | 2.95% | 2.91%, 0.10% /day | 3.03%, — |
|  | 3 × | 2.86% | 1.72%, 2.85% /day | 0.59%, 2.56% /day |
|  | MeTHF | 2.97% | 2.74%, 0.53% /day | 2.07%, 0.98% /day |
|  | 4 × | 2.92% | 1.06%, 4.55% /day | 0%, |
|  | MeTHF | 2.90% | 2.32%, 1.43% /day | 1.54%, 1.51% /day |
| Toluene | 2 × THF | 2.88% | 1.44%, 3.30% /day | 0.60%, 2.55% /day |
|  |  | 2.80% | 2.38%, 1.07% /day | 1.41%, 1.60% /day |
| Cumene | 2 × | 2.95% | 2.69%, 0.42% /day | 2.54%, 0.48% /day |
|  | MeTHF | 2.99% | 2.90%, 0.17% /day | 2.84%, 0.17% /day |
| MeTHF | MeTHF | 2.94% | 2.01%, 2.25% /day | 1.09%, 1.85% /day |
|  |  | 2.82% | 1.96%, 2.18% /day | 1.36%, 1.72% /day |

Figure 7:
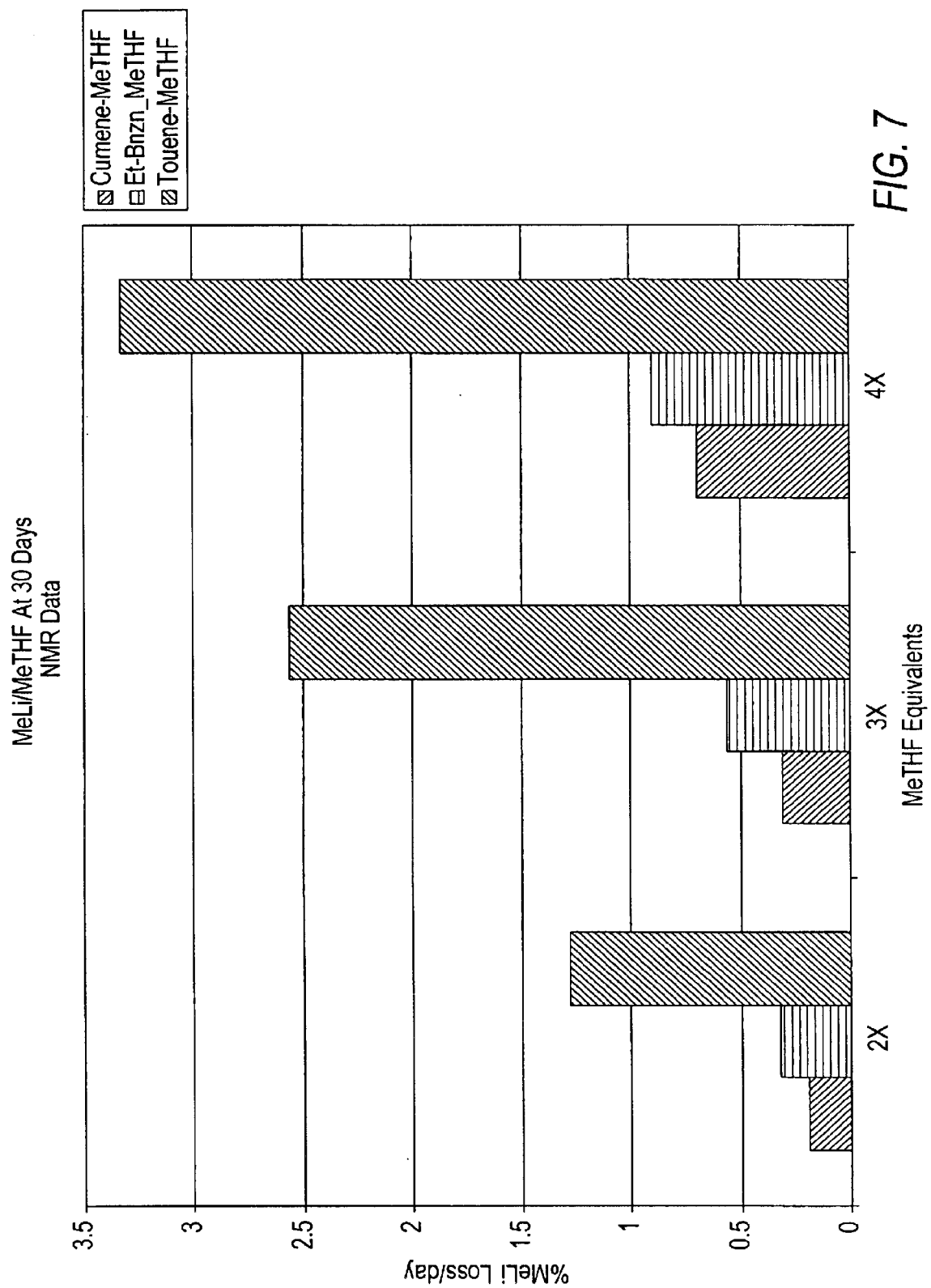
FIG. 7 is a graph showing the MeLi/MeTHF loss/day in various aromatic organic solvents and at various MeTHF equivalents.

FIG. 7 is a graph showing the average percent loss per day of MeLi for two, three and four equivalents of MeTHF in each of the aromatic solvents. It is obvious that for a given amount of MeTHF solutions in Cumene are more stable than those in Ethylbenzene which in turn are more stable than those in Toluene. In turn, for a given aromatic solvent two equivalents of MeTHF is more stable than three equivalents which is more stable than four equivalents of MeTHF. The cumulative result is that Cumene with two equivalents of MeTHF is the most stable formulation while four equivalents of MeTHF in Toluene is the least stable formulation using this particular ether.

Figure 8:
FIG. 8 if a graph showing MeLi loss per day for THF and MeTHF combinations.

FIG. 8 is a graph showing the dramatic difference between MeTHF and THF. The graph clearly shows that at 40° C., the formulations with THF have a daily percent loss of MeLi greater than twice that of those containing MeTHF. For a monometallic solution, MeTHF provides a significant increase in stability over THF.

It is claimed:

1. A methyllithium solution consisting essentially of methyllithium;
an aromatic solvent;
and from greater than 2 and up to 4 equivalents of methyltetrahydrofuran per mole of methyllithium.

2. The methyllithium solution of claim 1, wherein greater than 94 wt. % of methyllithium remains compared to the original amount of methyllithium in the solution after storage for 30 days at 40° C. as measured by $^1$H NMR spectroscopy.

3. The methyllithium solution of claim 1, comprising from 2.1 to 4 equivalents MeTHF.

4. A process for preparing methyllithium consisting essentially of preparing a mixture consisting essentially of lithium metal, methyltetrahydrofuran and an aromatic solvent, and adding chloromethane to react with the lithium, wherein greater than 2 and up to 4 equivalents of methyltetrahydrofuran are present per equivalent of MeLi produced by the reaction.

* * * * *